United States Patent [19]

Brochard et al.

[11] Patent Number: 4,950,784

[45] Date of Patent: Aug. 21, 1990

[54] PREPARATION OF O-ALKYL, S,S-DIALKYLPHOSPHORODITHIOATES

[75] Inventors: Jean-Michel Brochard, Alfortville; Francois Frisou, Suresnes; Pierre Le Roy, Thiais, all of France

[73] Assignee: Rhone-Poulenc Agrochimie, Lyons, France

[21] Appl. No.: 77,239

[22] Filed: Jul. 24, 1987

Related U.S. Application Data

[63] Continuation-in-part of Ser. No. 828,272, Feb. 11, 1986, abandoned.

[51] Int. Cl.$^5$ .................................................. C07F 9/17
[52] U.S. Cl. ....................................... 558/100; 558/99
[58] Field of Search ........................... 558/100, 208, 99

[56] References Cited

U.S. PATENT DOCUMENTS

| | | | |
|---|---|---|---|
| 3,112,244 | 11/1963 | Goyette | 558/208 |
| 3,839,510 | 10/1974 | Kudamatsu et al. | 558/208 |
| 4,596,796 | 6/1986 | Yamamoto et al. | 558/100 |

*Primary Examiner*—Anton H. Sutto
*Attorney, Agent, or Firm*—Burns, Doane, Swecker & Mathis

[57] ABSTRACT

The O-alkyl S,S-dialkylphosphorodithioates, e.g., ethoprophos, are facilely prepared, in improved yields and having great purity, by reacting an alkylphosphate dihalogenide, e.g., a dichloride, with a 1.5 to 8 mol excess of a thiol, in the presence of a 0.1 to 5 mol excess of an acid acceptor, with both molar excesses being per mole of said dihalogenide.

19 Claims, No Drawings

PREPARATION OF O-ALKYL, S,S-DIALKYLPHOSPHORODITHIOATES

CROSS REFERENCE TO RELATED APPLICATIONS

This application is a continuation-in-part of copending U.S. Ser. No. 828,272, filed Feb. 11, 1986, now abandoned.

BACKGROUND OF THE INVENTION

1. Field of the Invention:

The present invention relates to a novel process for preparing O-alkyl, S,S-dialkylphosphorodithioates, and, more especially, for preparing O-alkyl, S,S-dialkylphosphorodithioates by reacting an alkylphosphate dihalogenide with a thiol.

2. Description of the Prior Art:

O-ethyl, S,S-di-n-propylphosphorodithioate is known to this art as "ethoprophos" and is useful as both an insecticide and nematicide. The current success in the marketplace of compositions containing this compound for the control of insects and nematodes on plants has led to demand for the production of this compound in markedly increasing amounts.

British Patent No. 1,081,270 describes a process for preparing compounds of this type by reacting an alkylphosphate dihalogenide with a thiol (or mercaptan) in the presence of an acid acceptor, in accordance with the following reaction scheme:

$$R_1-O-P(X)_2 + 2HSR_2 + 2B \longrightarrow$$

$$R_1-O-P(SR_2)_2 + 2B/HX$$

wherein $R_1$ and $R_2$ are alkyl radicals and B is the acid acceptor. This latter material may be a mineral base such as an alkaline hydroxide in solid form, or an organic base such as a tertiary amine. This known process is carried out in a third organic solvent, such as an optionally chlorinated aliphatic or aromatic hydrocarbon, an ether, a ketone or a nitrile. When used for the preparation of ethophrophos, this prior art process provides a yield of 69% in the laboratory, which is far from satisfactory to be economically carried out on an industrial scale.

SUMMARY OF THE INVENTION

Accordingly, a major object of the present invention is the provision of an improved process for the preparation of the phosphorodithioic acid esters in increased yields and with enhanced product purity, which improved process does not require the use of a third, extraneous reaction solvent, is well adopted for being carried out on an industrial scale, and otherwise avoids those disadvantages and drawbacks to date characterizing the state of the art.

Briefly, the present invention features a process for the preparation of phosphorodithioic acid esters having the following general formula:

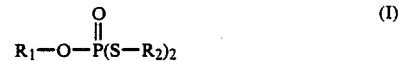
(I)

wherein $R_1$ is a lower alkyl radical preferably having from 1 to 4 carbon atoms, and, more preferably, having from 1 to 2 carbon atoms, and $R_2$ is a linear or branched chain lower alkyl radical preferably having from 1 to 5 carbon atoms and, more preferably, 3 or 4 carbon atoms, by reacting an alkylphosphate dihalogenide with a thiol, in the presence of an acid acceptor, and according to the following reaction sequence:

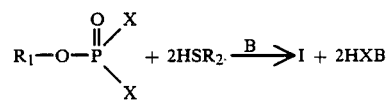

wherein $R_1$ and $R_2$ are as defined above, X is a halogen atom and preferably is a chlorine atom, and B represents an inorganic or organic acceptor, characterized in that the reaction is carried out in the presence of a 1.5 to 8 molar excess of thiol and a 0.1 to 5 molar excess of acid acceptor, per mol of the alkylphosphate dihalogenide.

DETAILED DESCRIPTION OF THE PREFERRED EMBODIMENTS OF THE INVENTION

More particularly according to the present invention, the molar excess of thiol over the acid acceptor advantageously ranges from 1 to 5 mols.

The subject process may be carried out in either of two embodiments, depending upon the nature of the acid acceptor.

In a first embodiment, the acid acceptor is a strong inorganic base in aqueous solution, in which case the excess of base typically ranges from 0.5 to 5 mols, and more preferably from 0.5 to 4 mols, again, per one mol of alkylphosphate dihalogenide. Stated differently, the molar excess of thiol over the base generally ranges from about 1 to 4 mols. It should be noted that in this embodiment the reaction medium comprises one organic phase and one aqueous phase. As examples of suitable inorganic bases, the alkali metal, e.g., sodium or potassium, and alkaline earth metal hydroxides are representative.

In a second embodiment of the invention, the acid acceptor is a strong organic base, preferably a tertiary amine such as, for example, a trialkylamine, the alkyl radicals of which advantageously contain from 1 to 4 carbon atoms, and particularly triethylamine. Further, this organic base is used in an excess of about 0.1 to 0.5 mol per one mol of alkylphosphate dihalogenide. Moreover, the reaction is carried out in the presence of a molar excess of thiol of from about 1.5 to 8 mols per one mol of the alkylphosphate dihalogenide. In other words, the molar excess of thiol over the organic base ranges from about 2.3 to 5 mols. It should be noted that in this embodiment of the invention, the reaction medium comprises essentially one anhydrous organic phase.

The process according to the invention has the advantage of obviating the need for a third solvent which would necessitate a supplementary separation step, and further enables the subject compounds to be produced in greatly improved yields and with higher degrees of purity.

In order to further illustrate the present invention and the advantages thereof, the following specific examples are given, it being understood that same are intended only as illustrative and in nowise limitative. In said examples to follow, the structures of the reaction products were confirmed by NMR spectography.

EXAMPLE 1

Into a 1.5 l reactor, equipped with a double cooling jacket in which flowed a fluid to dissipate heat, 246.3 g n-propylmercaptan, then 238.8 g of an aqueous solution containing 22% sodium hydroxide were poured, under a nitrogen atmosphere, while maintaining the temperature of the reaction medium at 0° C.

To this mixture, 79.9 g O-ethylphosphate dichloride were added at a temperature maintained at from 0° C. to 5° C.

The reaction medium was stirred at 20° C. for 1 hour.

After decantation and separation of the phases, the organic phase was washed with water and n-propylmercaptan evaporated off under vacuum. The residue contained 110.1 g of O-ethyl, S,S-di-n-propyldithiophosphate, i.e., a yield of 91% of theory (in mol vis-a-vis the ethylphosphate dichloride).

EXAMPLE 2

Into a 1.5 l reactor equipped with a double cooling jacket in which flowed a heat exchange fluid to dissipate heat, 293.1 g of sec-butylmercaptan, then 365.5 g of an aqueous solution containing 22% sodium hydroxide were poured, under a nitrogen atmosphere, while maintaining the temperature of the reaction medium at 0° C.

The procedure as set forth in Example 1 was then utilized.

The residue, after separation and evaporation under vacuum, contained 96.6 g of O-ethyl S,S-di-secbutyldithiophosphate, i.e., 73% of theory (in mol vis-a-vis the ethylphosphate dichloride).

EXAMPLE 3

Into a 2 l reactor equipped with a double cooling jacket in which flowed a fluid to dissipate heat, 457.3 g (i.e., 6 mols) of 94% n-propyl mercaptan, and then 163.1 g (i.e., 1 mol) of 93% O-ethylphosphate dichloride were added, under a nitrogen atmosphere.

The reaction medium was cooled to a temperature of from −5° to −10° C. Then, while maintaining same at a temperature of from −5° to 0° C., 222.2 g (i.e., 2.2 mols) of 99% triethylamine were progressively poured therein over a period of 1 hr, 30 min, and the medium was maintained under stirring for 3 hr, 30 min, at a temperature of from 5° to 10° C. 244.5 g of an aqueous solution of 24.5 g of hydrochloric acid (38%) in 220 g water were then added. After decantation and phase separation, the organic phase was washed with water and n-propylmercaptan was evaporated off under vacuum.

The residue contained 226.2 g O-ethyl S,S-di-n-propyldithiophosphate (purity 95.5%), i.e., a yield of 96.2% (in mol vis-a-vis the ethylphosphate dichloride).

EXAMPLE 4

The procedure of Example 3 was used, except for the replacement of n-propylmercaptan with 585 g (i.e., 6.5 mols) of sec-butyl mercaptan.

After the triethylamine was added, the medium was maintained under stirring for 5 hours at a temperature of 5° C.

Under these conditions, O-ethyl S,S-di-secbutyldithiophosphate was obtained in a yield of 50% and a purity of 95%.

EXAMPLE 5

Into a 1.5 l reactor equipped with a double cooling jacket in which flowed a fluid to dissipate heat, 507 g (i.e., 5.6 mols) of sec-butyl mercaptan, and then 75 g of sodium hydroxide pellets, were introduced with strong stirring, whereby the temperature of the reaction mass was raised to 80° C. Once the medium was quite fluid, the temperature was lowered to 10° C. While maintaining this temperature, 122 g of O-ethylphosphate dichloride were then added dropwise. The reaction medium was then stirred for 1 hour at a temperature of 10° C., with 250 g water and then 32 g of an aqueous solution of hydrochloric acid (37%) being added.

After decantation and phase separation, the organic phase was washed with water and sec-butylmercaptan was evaporated off under vacuum.

The residue contained 245.7 g O-ethyl S,S di-sec-butyldithiophosphate (purity 97%), i.e., a yield of 91% (in mol vis-a-vis ethylphosphate dichloride).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an O-alkyl, S,S-dialkylphosphorodithioate having the general formula (I):

wherein $R_1$ is a lower alkyl radical, and $R_2$ is a linear or branched chain lower alkyl radical, comprising reacting an alkylphosphate dihalogenide with a 1.5 to 8 molar excess of thiol, per mole of alkylphosphate dihalogenide, in the presence of a 0.1 to 5 molar excess of an acid acceptor, also per mole of alkylphosphate dihalogenide, and according to the reaction scheme:

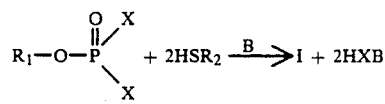

wherein $R_1$, $R_2$ and (I) are as above defined, X is a halogen, and B is an inorganic or organic acid acceptor.

2. The process as defined by claim 1, wherein $R_1$ is a lower alkyl radical having from 1 to 4 carbon atoms, and $R_2$ is a linear or branched chain lower alkyl radical having from 1 to 5 carbon atoms.

3. The process as defined by claim 2, wherein $R_1$ has 1 or 2 carbon atoms, and $R_2$ has 3 or 4 carbon atoms.

4. The process as defined by claim 2, wherein X is chlorine.

5. The process as defined by claim 2, wherein B is a strong inorganic base in aqueous solution, and is present in a 0.5 to 5 mol excess.

6. The process as defined by claim 5, wherein B is an alkali or alkaline earth metal hydroxide.

7. The process as defined by claim 6, wherein B is sodium or potassium hydroxide.

8. The process as defined by claim 2, wherein B is a strong organic base, and is present in a 0.1 to 0.5 mol excess.

9. The process as defined by claim 8, wherein said strong organic base is a tertiary amine.

10. The process as defined by claim 9, wherein said tertiary amine is a trialkylamine, the alkyl radicals of which have from 1 to 4 carbon atoms.

11. The process as defined by claim 10, wherein said tertiary amine is triethylamine.

12. The process as defined by claim 5, wherein the reaction medium comprises an organic phase and an aqueous phase.

13. The process as defined by claim 8, wherein the reaction medium comprises an anhydrous organic phase.

14. The process as defined by claim 8, wherein the thiol is present in a 2.5 to 4.5 molar excess.

15. The process as defined by claim 1, wherein $R_1$ is ethyl, $R^2$ is n-propyl, and x is a chlorine atom.

16. The process as defined by claim 1, wherein $R_1$ is ethyl, $R^2$ is branched butyl, and X is a chlorine atom.

17. The process as defined by claim 16, wherein $R^2$ is sec-butyl.

18. The process as defined by claim 5, wherein B is present in a 0.5 to 3 molar excess, and the thiol is present in a 1.5 to 7 molar excess.

19. The process as defined by claim 5, wherein B is present in a 1.5 to 4 molar excess, and the thiol is present in a 3.5 to 8 molar excess.

* * * * *